(12) United States Patent
Jensen et al.

(10) Patent No.: US 9,642,598 B2
(45) Date of Patent: May 9, 2017

(54) ULTRASOUND IMAGING CONSOLE

(75) Inventors: Henrik Jensen, Bagsvaerd (DK);
Robert Harold Owen, Stenlose (CA);
Lars Nordahl Moesner, Glostrup (DK)

(73) Assignee: B-K Medical Aps, Herlev (DK)

( * ) Notice: Subject to any disclaimer, the term of this patent is extended or adjusted under 35 U.S.C. 154(b) by 192 days.

(21) Appl. No.: 14/344,356

(22) PCT Filed: Sep. 12, 2011

(86) PCT No.: PCT/IB2011/002119
§ 371 (c)(1),
(2), (4) Date: Mar. 12, 2014

(87) PCT Pub. No.: WO2013/038217
PCT Pub. Date: Mar. 21, 2013

(65) Prior Publication Data
US 2014/0343429 A1    Nov. 20, 2014

(51) Int. Cl.
*A61B 8/00* (2006.01)
*A61B 8/08* (2006.01)
*A61B 8/14* (2006.01)
*G01S 15/89* (2006.01)

(52) U.S. Cl.
CPC ............ *A61B 8/4477* (2013.01); *A61B 8/145* (2013.01); *A61B 8/4209* (2013.01); *A61B 8/4444* (2013.01); *A61B 8/4483* (2013.01); *A61B 8/5207* (2013.01); *A61B 8/56* (2013.01); *A61B 8/4245* (2013.01); *A61B 8/44* (2013.01); *G01S 15/8909* (2013.01)

(58) Field of Classification Search
None
See application file for complete search history.

(56) References Cited

U.S. PATENT DOCUMENTS 4,726,230 A    2/1988    Yoshikawa et al.
4,819,650 A    4/1989    Goldstein
5,673,698 A *  10/1997   Okada et al. ................. 600/447
(Continued)

FOREIGN PATENT DOCUMENTS

EP      2036500 A      3/2009
WO      2004064614 A2  8/2004

OTHER PUBLICATIONS

Zero insertion force by. Wikipedia, Pub. Aug. 10, 2010 online at https://en.wikipedia.org/wiki/Zero_insertion_force, accessed Aug. 24, 2105.*

(Continued)

*Primary Examiner* — Katherine Fernandez
*Assistant Examiner* — Michael Kellogg
(74) *Attorney, Agent, or Firm* — Anthony M. Del Zoppo, III; Driggs, Hogg, Daugherty & Del Zoppo, Co., L.P.A.

(57) ABSTRACT

An ultrasound imaging system includes a beamformer (104) configured to beamform ultrasound signals. The beamformer includes input/output (110) configured to at least receive ultrasound signals. The ultrasound imaging system further includes a first ultrasound probe connector (128) and a second ultrasound probe connector (128). The ultrasound imaging system further includes a switch (134) that concurrently routes ultrasound signals concurrently received via the first ultrasound probe connector and the second ultrasound probe connector to the beamformer, which processes the ultrasound signals.

17 Claims, 6 Drawing Sheets

(56) References Cited

U.S. PATENT DOCUMENTS

| | | | |
|---|---|---|---|
| 6,045,508 A | 4/2000 | Hossack et al. | |
| 7,090,643 B2 | 8/2006 | Fidel et al. | |
| 2005/0203399 A1* | 9/2005 | Vaezy | A61B 8/08 600/439 |
| 2010/0022884 A1 | 1/2010 | Ustuner et al. | |

OTHER PUBLICATIONS

International search report for PCT/IB2011/002119 published as WO 2013/038217.
Lindsey, et al, The Ultrasound Brain Helmet: New Transducers and Volume Registration for In Vivo Simultaneous Multi-Transducer 3-D Transcranial Imaging, IEEE Transactions on Ultrasonics, Ferroelectrics, and Frequency Control, Vo. 58, No. 6, Jun. 2011.
Chinese Office Action dated Jun. 18, 2015, for Chinese application No. 201180074093.7.

\* cited by examiner

ULTRASOUND IMAGING CONSOLE

RELATED APPLICATION

This application is a national filing of PCT application Serial No. PCT/IB2011/002119, filed Sept. 12, 2011, published as WO/2013/038217 on Mar. 21, 2013.

TECHNICAL FIELD

The following generally relates to ultrasound (US) imaging and more particularly to an US console configured to concurrently scan using multiple probes respectively connected to different probe connectors of the console and/or multiple transducer arrays of a single probe connected to a connector of the console.

BACKGROUND

An ultrasound (US) imaging system generally includes a console with a connector(s) configured to receive a complementary connector of an ultrasound probe having a transducer array. The transducer array has been used to transmit ultrasound signals and acquire ultrasound echoes corresponding to a plane (e.g., axial) of an organ(s) and/or structure(s) (e.g., a biopsy needle) in the body. In B-mode imaging, the echoes have been processed to generate scanlines, which have been used to generate a scanplane (or 2D image of the plane), which can be visually presented via a display.

In order to additionally view a plane in another orientation (e.g., sagittal), the user has to move the probe to the other orientation and perform a scan at the other orientation. In response to moving the probe and scanning in the other orientation, the displayed image in the first orientation is replaced by another image from the other orientation. In order to concurrently utilize the images from both orientations, the clinician has to make a mental image of the first image (i.e., memorize it) and then mentally construct an image based on the mental image and the displayed second image.

Another approach includes using a second probe connected to a second connector of the console. Unfortunately, ultrasound consoles only scan on one connector at a time. As such, images of different planes are acquired at different times and have to be mentally combined to construct an image. Another approach includes using a biplane probe, which is a probe that includes two arrays angularly arranged with respect to each other to acquire data from different planes (e.g., axial and sagittal planes). With a biplane probe, either both arrays have a reduced set of elements such that the total number of elements is the same as a single array probe or a multiplexer is used to alternately operate the arrays.

SUMMARY

Aspects of the application address the above matters, and others.

In one aspect, an ultrasound imaging system includes a beamformer configured to beamform ultrasound signals. The beamformer includes input/output configured to at least receive ultrasound signals. The ultrasound imaging system further includes a first ultrasound probe connector and a second ultrasound probe connector. The ultrasound imaging system further includes a switch that concurrently routes ultrasound signals concurrently received via the first ultrasound probe connector and the second ultrasound probe connector to the beamformer, which processes the ultrasound signals.

In another aspect, a method includes routing a first signal between a first transducer array of a first ultrasound probe connected to a first connector of the ultrasound console and a beamformer of the ultrasound console through a switch of the ultrasound console and routing, concurrently with routing the first signal, a second signal between a second transducer array of a second ultrasound probe connected to a second connector of the ultrasound console and the beamformer through the switch.

In another aspect, an ultrasound imaging system includes a beamformer, which includes transmit circuitry configured to generate an ultrasound transducer element excitation signal, receive circuitry configured to process an ultrasound echo and input/output configured to transmit the ultrasound transducer element excitation signal and receive the ultrasound echo. The ultrasound imaging system further includes at least one ultrasound probe connector respectively configured to receive a complementary connector of an ultrasound probe and having at least two transducer arrays. The ultrasound imaging system further includes a switch that routes signals between the at least two transducer arrays and the input/output, wherein the switch concurrently routes a first signal between a first of the at least two transducer arrays and the beamformer and a second signal between a second of the at least two transducer arrays and the beamformer.

In another aspect, a method of ultrasound tracking includes concurrently employing at least two ultrasound probes connected to two different connectors of an ultrasound console in a medium, wherein the at least two ultrasound probes share input/output channels of the ultrasound console such that a first set of the channels is used by a first of the at least two probes concurrently while a second different set of the channels is used by a second of the at least two probes. The method further includes employing data received by the at least two probes to estimate a relative position of the at least two probes.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
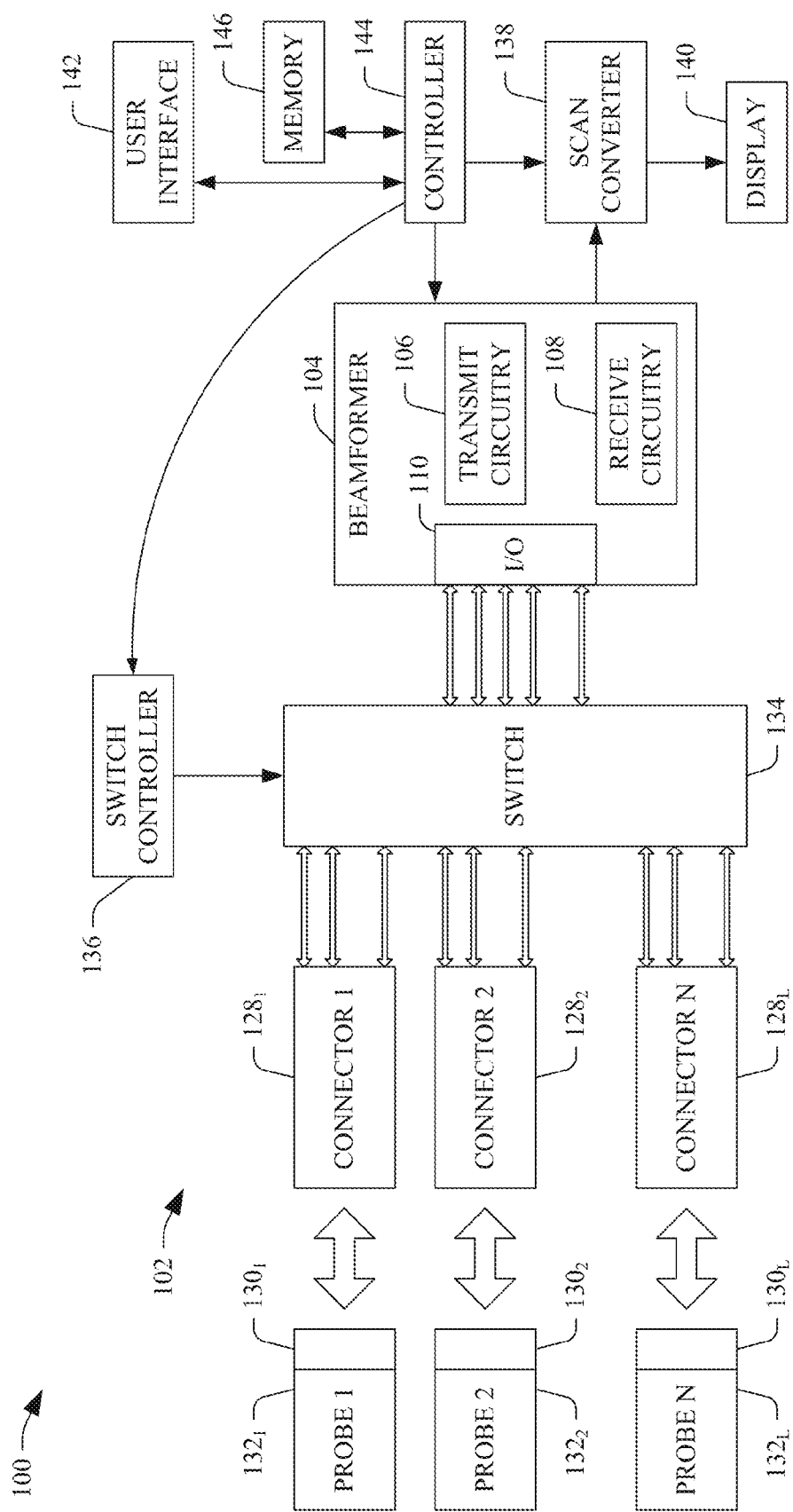
FIG. 1 schematically illustrates an example imaging system configured to concurrently scan with multiple probes respectively connected to different connectors of the console.

FIG. 1 schematically illustrates an imaging system 100, such as an ultrasound imaging system, which includes a console 102.

The console 102 includes a beamformer 104 with transmit circuitry 106 and receive circuitry 108. In another embodiment, the transmit circuitry 106 and the receive circuitry 108 are not part of the same beamformer. The transmit circuitry 106 generates electrical signals which control transducer element phasing and/or time of actuation, which allows for steering and/or focusing an ultrasound beam from predetermined origins and at predetermined angles.

The receive circuitry 108 processes received ultrasound echoes. For B-mode applications, this has included delaying and summing echoes to produce a sequence of focused, coherent echo samples along focused scanlines of a scanplane. The receive circuitry 108 may also be configured to process the scanlines to lower speckle and/or improve specular reflector delineation via spatial compounding and/or perform other processing such as FIR filtering, IIR filtering, etc.

The beamformer 104 also includes I/O 110, including a plurality of channels (not visible), for conveying the electrical signals and receiving the echoes.

The imaging system 102 further includes a plurality of connectors $128_1$, $128_2$, ..., $128_L$ (or connectors 128), where L is an integer equal to or greater than two. The connectors 128 each include elements (not visible) such as pins, sockets, etc. that mechanically and/or electrically connect with complementary elements (not visible) of probe connectors $130_1$, $130_2$, ..., $130_L$ (or probe connectors 130) of ultrasound probes $132_1$, $132_2$, $132_L$ (or ultrasound probes 132).

An individual one of the probes 132 may include one or more transducer arrays, each having one or more transducer elements such as 16, 64, 128, 196, 256, and/or other number of transducer elements. Individual arrays may include linear, curved, and/or rotary transducer arrays, and the different arrays can be employed individually, simultaneously or in an interleaved manner to acquire data.

The imaging system 102 further includes a switch 134. One side of the switch 134 is in electrical communication with the elements (not visible) of the connectors 128, and the other side of the switch 134 switch is in electrical communication with the I/O 110 of the beamformer 104. Generally, the I/O 110 includes fewer or the same number of channels (not visible) as the aggregate number of the elements (not visible) of all the connectors 128. The I/O 110 may have less, the same number or more channels than there are elements in any one of the individual connectors 128. Where the I/O 110 has fewer channels than there are elements in any one of the individual connectors 128, a fraction of the channels can be used on one connector 128 with the other channels used on one or more other of the connectors 128.

As described in greater detail below, the switch 134 routes signals between the beamformer 104 and multiple connectors 128 as if the elements (not visible) of the connectors 128 were part of a single connector and the I/O 104 had a number of channels (not visible) equal to that of the elements of the multiple connectors 128 such that any number of probes 132 can be concurrently employed by the console 102, where individual channel (not visible) of the I/O 104 are switched between connector elements (not visible) using fast switching, for example, solid state multiplexers or the like.

In one non-limiting instance, this includes changing the state of the switch 134 during a transmission, so one channel transmits with one element and receives with another element from the same or a different connector 128. In another non-limiting instance, the state of the switch 134 is changed so that one channel is used to transmit on different elements in the same transmission and/or to receive from different elements during the same transmission, for example, when using neighboring elements in parallel or otherwise. Still other instance are contemplated herein. It is to be appreciated that the connectors 128 can also be operated alternately and/or in an interleaved manner.

A switch controller 136 transmits signals to the switch 134, which control the switching of the switch 134. Such control can be based on a selected imaging protocol, use of the probes 132 by an operator, and/or otherwise.

A scan converter 138 converts raw and/or processed echoes to generate data for display, for example, by converting the data to the coordinate system of the display. The scan converter 116 can be configured to employ analog and/or digital scan converting techniques. A display 140 can be used to present the scan converted data, including multiple images and simultaneous updates of the images.

A user interface 142 includes various input and/or output devices, for example, to select a data processing and presentation mode, a data acquisition mode (e.g., B-mode), initiate scanning, etc. The user interface 142 may include buttons, knobs, a keypad, a touch screen, etc. The user interface 122 may also include various types of visual (e.g., LCD, LED, etc.) and/or audible displays.

A main controller ("controller") 144 includes a processor (not visible) or the like which executes one or more instructions embedded or encoded on computer readable medium such as physical memory 146. The processor can additionally or alternatively execute instructions carried by a carrier wave, a signal or other transitory medium. The controller 138 can control the beamformer 104, the switch controller 136, the scan converter, and/or the user interface.

Figure 2:
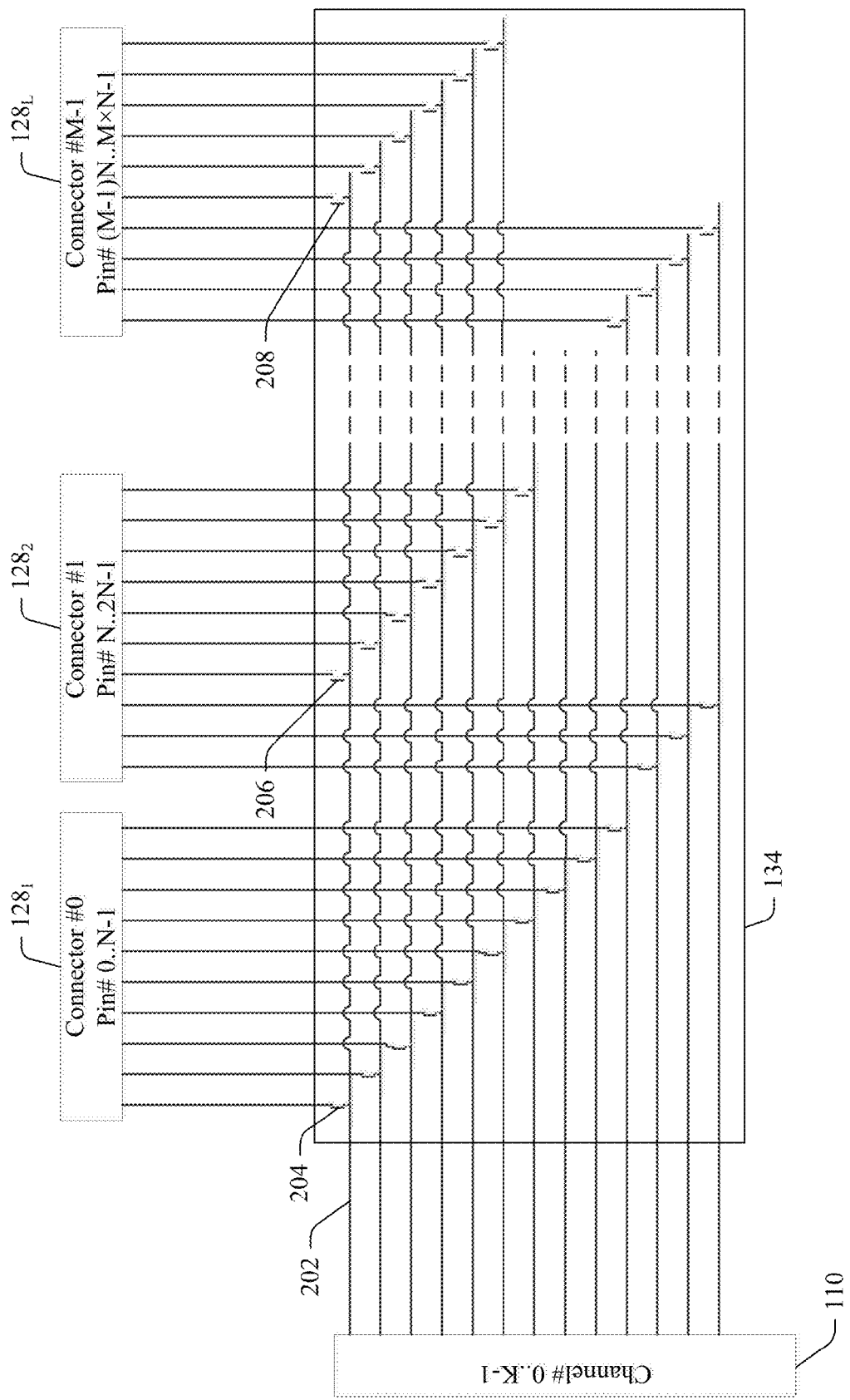
FIG. 2 schematically illustrates an example switch of the console configured to switch channels of the console amongst the multiple probes.

FIG. 2 schematically illustrates a non-limiting example of the switch 134 in connection with the I/O 110 of the beamformer 104 and the connectors 128. In this example, the I/O 110 includes k channels, channel 0 ... channel K−1. The connector $128_1$ includes N pins (i.e., pin 0 ... N−1), the connector $128_2$ includes N pins (i.e., pin N ... 2N−1), and the connector $128_L$ includes N pins (i.e., pin (M−1)N M×N−1). The total number of pins is M×N. In another embodiment, two or more of the connectors 128 may include a different number of pins.

As shown, an electrical pathway 202 alternately electrically connects channel 0 of the I/O 110 to pin 0 of connector $128_1$ through a switch 204, to pin N+3 of connector $128_2$ through a switch 206, ..., and to pin (M−1)×5 of the connector $128_3$ through a switch 208. In the illustrated embodiment, the switch 204 is closed, establishing an electrical connection between channel 0 and pin 0, and switches 206, ..., 208 are open such that no electrical connection is established between channel 0 and pin N+3 or pin (M−1) N+5. Other electrical pathways similarly connect other channels of the I/O 110 with other pins of the connector $128_2$ ... connector $128_1$.

Where the next connector 128 to communicate over channel 0 is connector $128_2$, the switch controller 136 (FIG. 1) sends a signal to the switch 134 which causes switch 204 to open and switch 206 to close such that an electrical connection is established between channel 0 and pin N+3, and no electrical connection exists between channel 0 and pin 0 or channel 0 and pin (M−1)N+5. Where the next connector 128 to communicate over channel 0 is connector 128₃, the switch controller 136 (FIG. 1) sends a signal to the switch 134 which causes switch 206 to open and switch 208 to close such that an electrical connection is established between channel 0 and pin (M−1)N+5, and no electrical connection exists between channel 0 and pin 0 or channel 0 and pin N+3.

In the illustrated example, all the pins of the connector 128₁ are connected to the I/O 110 and a sub-set of the pins of the connector 128₂ are connected to the I/O 110. In another instance, all the pins of the connector 128₂ are connected to the I/O 110 and a sub-set of the pins of the connector 128₁ are connected to the I/O 110. In yet another instance, some of the pins of one or more of the other connectors 128 are connected to the I/O 110. Generally, through one or more predetermined switching patterns, pins of two to M of the connectors 128 can be concurrently connected to the I/O 134 and concurrently employed to concurrently scan.

Suitable connectors 128 include connectors with pins that generally are inaccessible such as zero insertion force (ZIF) integrated circuit (IC) sockets, low insertion force (LIF) IC sockets, and/or other connectors.

There are a number of situations where concurrently employing two or more of the probes 132 using the system 100 can add value to an examination. For example, with lithotripsy, during treatment using a first one of the probes 132, if the operator is unsure whether there really is a kidney stone at a target point, a second different one of the probes 132 can be concurrently used to verify the presence of the stone at the target point.

This can save time and improve certainty relative to a configuration in which the switch 134 is omitted and the treatment is interrupted so that a second probe can be used to verify presence of the stone. Another example is the combination of abdominal and endo scanning where the endo scanning is used to monitor cryo-therapy or HIFU. Generally, the system 100 can be used for any application in which concurrent use of multiple probes maybe of interest.

Figure 3:
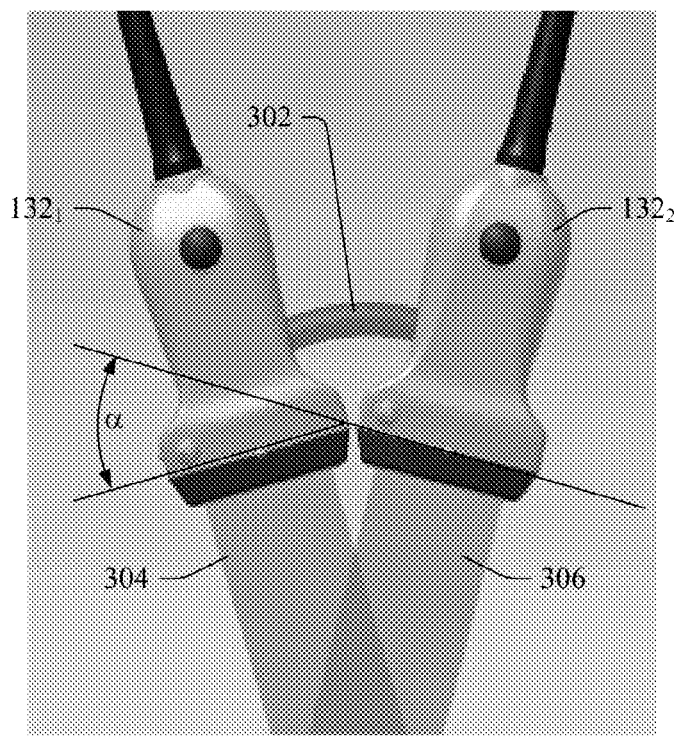
FIG. 3 illustrates a support configured to support multiple probes.

FIG. 3 shows an example in which a probe support 302 supports two probes 132₁ and 132₂ at fixed relative positions that are angularly offset from each other by an angle α. In other embodiments, the support 302 can support more than two of the probes 132. Where the support 302 is configured to hold the probes 132 such that their image planes 304 and 306 coincide, compounding can be achieved with large compound angles, or a limited degree of tomography can be achieved if the angle a is large enough that the elements in one of the probes 132 is within sight of the elements of the other of the probes 132.

For tomography, the support 302 can extend such that the two probes 132₁ and 132₂ can be angularly oriented with respect to each other (e.g., 180 degrees apart) such that the transducers are face-to-face with a suitable distance there between. Tomography can be used to provide velocity and attenuation maps, which are weakly correlated to the scattering information that is used to form B-mode images, so it provides complementary information, and potentially the velocity map can be used to improve the focusing in the B-mode image.

If the axes of the two probes 132₁ and 132₂ are near orthogonal (e.g., α∼90 degrees), side scattering can be measured. Where the support 302 is configured to hold the two probes 132₁ and 132₂ such that their transducers are held with the same orientation but with parallel or almost parallel image planes, flow or motion normal to the image plane can be measured using Doppler techniques or tracking methods.

Although the illustrated two probes 132₁ and 132₂ are shown as the same type of probes, it is to be appreciated that the two probes 132₁ and 132₂ can be different types of probes. The support 302 may be configured to support the probes 132 at designated static positions or one or more of the probes 132 can be manually placed at a position of interest and removeably secured in place. A robot, operator, and/or holding device can be used to hold a probe 132 in place.

Concurrently using multiple probes 132 for spectral Doppler allows for simultaneous Doppler imaging of different organs, which allows the propagation speed of the pulsations to be measured, which is different from measuring flow velocity.

Figure 4:
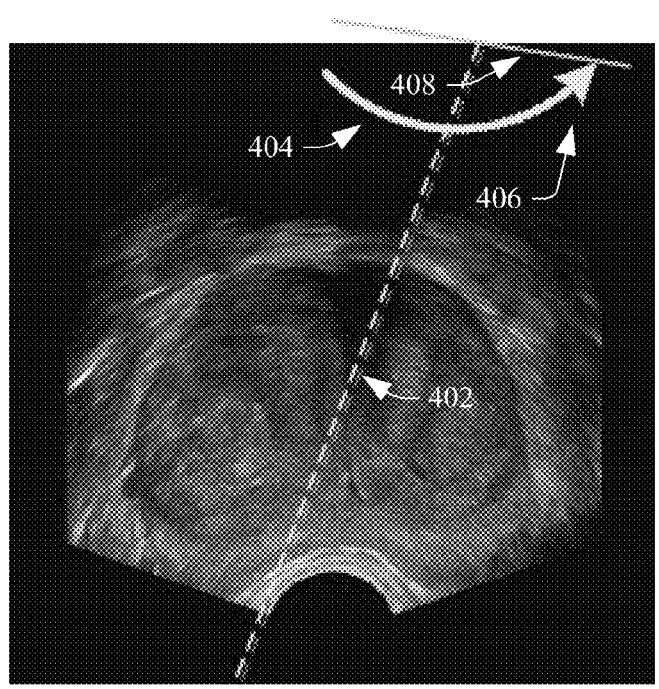
FIG. 4 illustrates an image and indicia superimposed thereon showing what to do to make the planes coincide.

Concurrent free hand scanning with two or more of the probes 132 (scanning without using the support 302 to hold the probes 132 at fixed relative positions) can be achieved with having each of the probes 132 track the position of the other probe 132. For visual presentation or display, the intersecting image planes can be identified or highlighted using as a dotted line, a dashed line 402 as shown in FIG. 4, and/or other line and/or other indicia.

Additionally or alternatively, a distance between planes can be shown through use of a bar, a circle and/or other indicia, within or outside of the image area. Additionally or alternatively, indicia showing what to do to make the planes coincide as a displacement direction and a rotation can be displayed. For example, as shown in FIG. 4, an arc 404 with an arrow tip 406 can be used to indicate rotation around a transducer axis 408.

Another option is to show both images in pseudo 3D (e.g., 2D images shown in 3D space) in separate views. In the case of a tracked freehand transducer for lithotripsy, the location and offset to the shock wave focus can be superimposed on the image from the free hand probe 132. The position can be shown as a crosshair used for targeting in combination with an indication of the offset between the image plane and the shock wave focus.

If there is no external tracking, the probes 132 can be used to estimate their relative positions. This is done by measuring the time of flight from a set of elements on one transducer probe 132 to another set of elements on another transducer probe 132. In a homogeneous medium, this can be achieved through triangulation. In an inhomogeneous medium, the propagation path may not be straight lines and the propagation velocity may not be the same, but due to the principle of reciprocity the path in both directions is the same, and therefore the tracking of a common region of interest in images made with the transducer probes 132 is more accurate than a geometrically accurate tracking system would provide.

Figure 5:
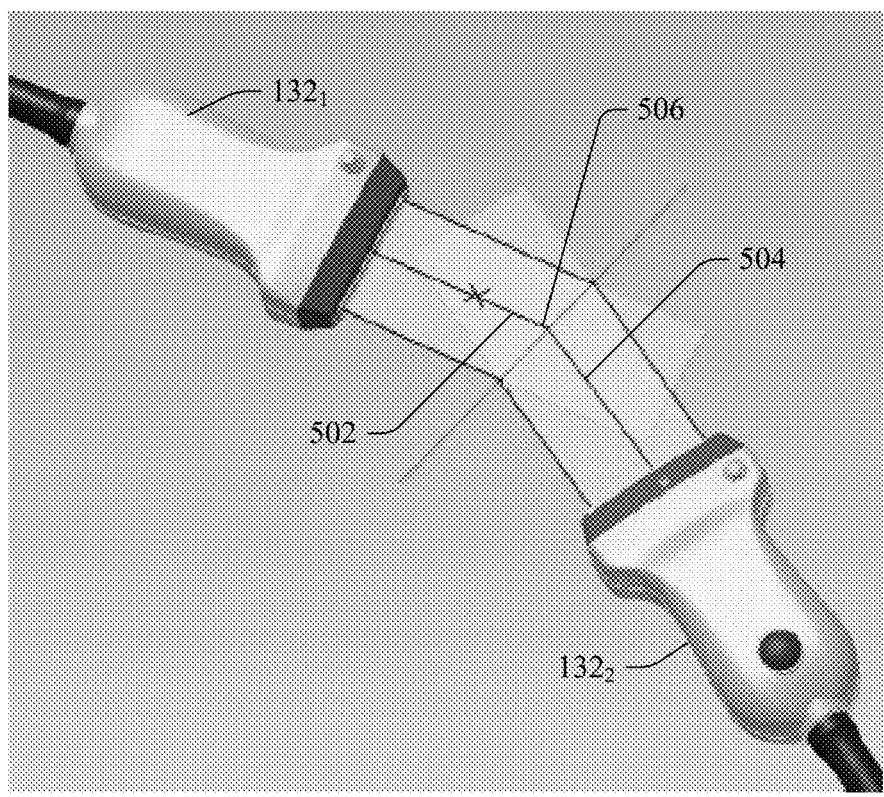
FIG. 5 illustrates two probes aligned such that their center scan lines coincide.

As an example, and as shown in connection with FIG. 5, where the two transducer probes 132₁ and 132₂ are scanning in two different media with different sound velocities causing refraction at the interface between the two media, the probes 132₁ and 132₂ can be aligned such that the center scan lines 502 and 504 coincide at a region 506. The propagation along the center line is substantially the same in both directions. Therefore, the propagation time to a point on that scan line can be estimated accurately from both transducers as the sum is known. This also holds for the lateral position.

If a point is on the center scan line this is true for both transducer probes 132₁ and 132₂. If the point is not on the center scan line, the two probes 132₁ and 132₂ will largely agree on the lateral position even though the scan line is not straight, so the error caused by refraction is eliminated and the residual error is small. As such, tracking with the system 100 will to some degree compensate for inhomogeneous velocity in the media between the transducer probes 132₁ and 132₂ and thereby be more accurate than other methods without tracking.

On two linear array transducers the triangulation alone cannot align the mutual roll angles. This can be overcome by optimizing the signal strength as it is very dependent on the roll angle. Alternatively the transducers can have a single transducer element that is not in-line with the transducer array, to provide this additional information.

Variations are Contemplated.

Figure 6:
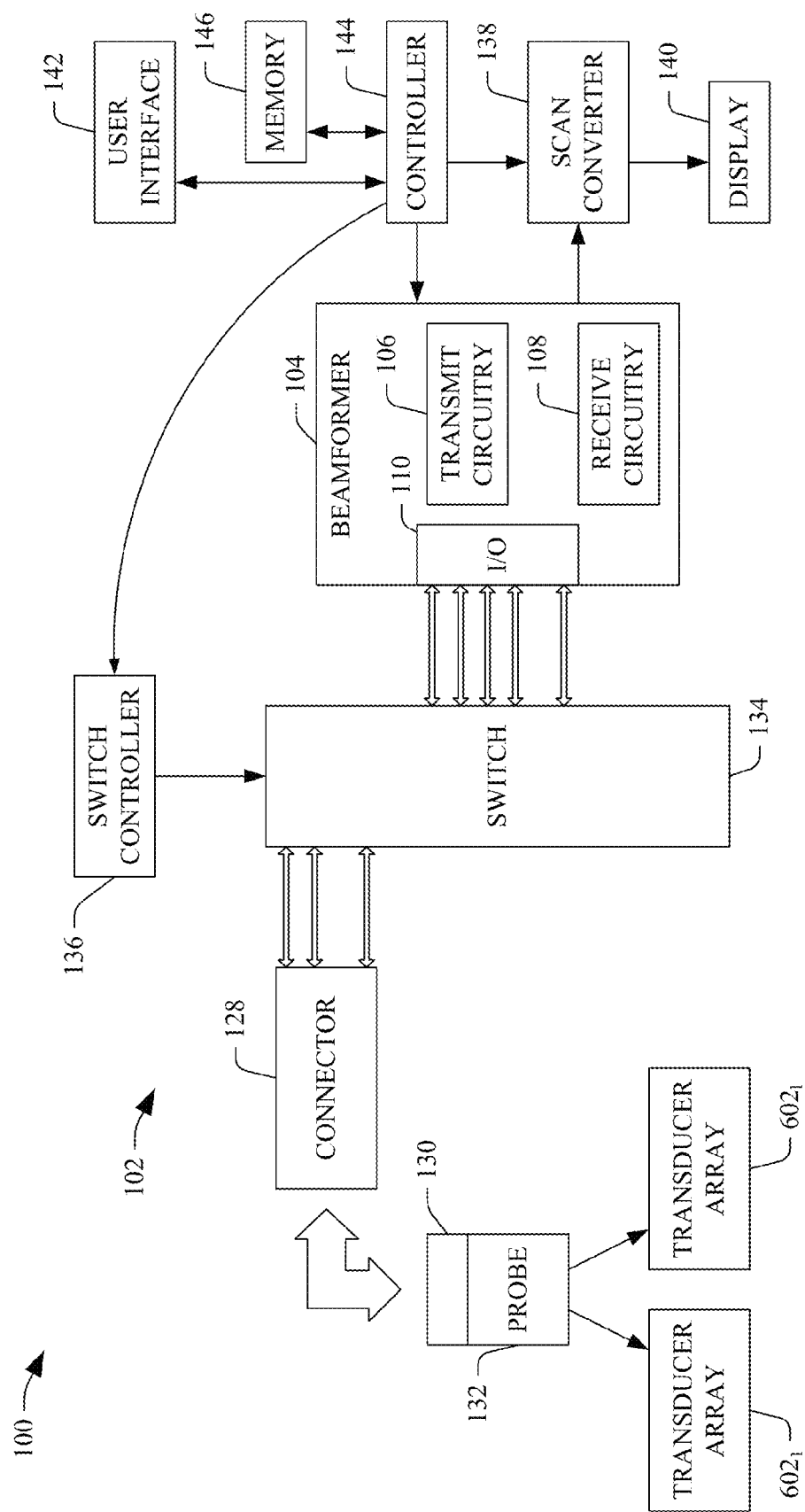
FIG. 6 schematically illustrates an example imaging system configured to concurrently scan with multiple transducer arrays of a single probes.

FIG. 6 shows a variation in which a single probe 132 having multiple transducer arrays 602₁ . . . 602ⱼ (transducer arrays 602), where j is an integer equal to or greater than one, is connected to a single connector 128. In this instance, the different transducer arrays 602 can be employed as described herein in a similar manner as the different probes 132 in that multiple ones of the transducer arrays 602 can be concurrently employed via suitable switching via the switch 134 between the connector 128 and the I/O 110.

In another variation, the embodiments of FIGS. 1 and 6 are combined in that one or more of the individual probes 132 of FIG. 1 can include two or more transducer arrays 602 as shown in FIG. 6. In this instance, the switch 134 switches the channels of the I/O 110 such that two or more probes 132 and/or two or more transducer arrays of two or more probes are concurrently employed.

Figure 7:
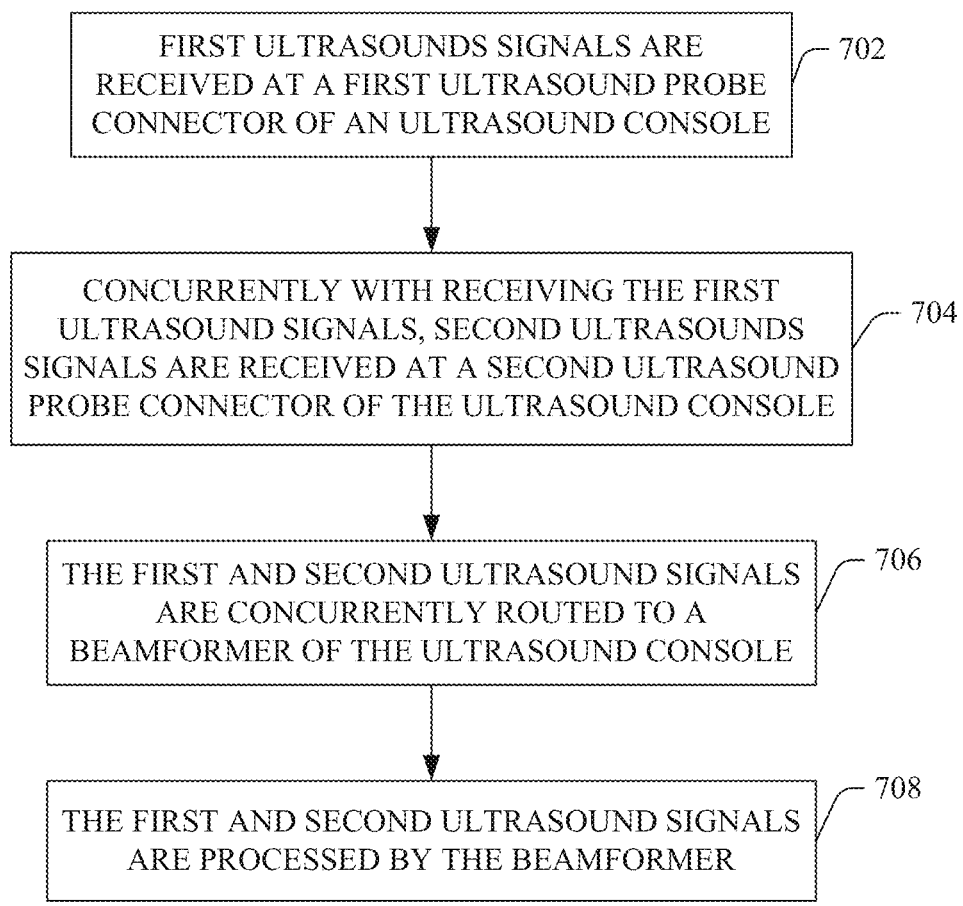
FIG. 7 illustrates an example for concurrently scanning with multiple transducer probes of an ultrasound console.

FIG. 7 illustrates a method for concurrently scanning with multiple transducer probes of an ultrasound console.

It is to be appreciated that the order of the method acts is provided for explanatory purposes and is not limiting. As such, one or more of the following acts may occur in a different order. Furthermore, one or more of the following acts may be omitted and/or one or more additional acts may be added.

At 702, first ultrasound signals are received at a first ultrasound probe connector of the ultrasound console. The first ultrasound signals are received from a first ultrasound probe installed in the first ultrasound probe connector.

At 704, second ultrasound signals are received, concurrently with act 702, at a second ultrasound probe connector of the ultrasound console. The second ultrasound signals are received from a second ultrasound probe installed in the second ultrasound probe connector.

At 706, the first and second ultrasound signals are concurrently routed, via a switch, to a beamformer of the console.

At 708, the first and second ultrasound signals are processed by the beamformer. It is to be appreciated that the methods herein may be implemented by one or more processors executing computer executable instructions stored, encoded, embodied, etc. on computer readable storage medium such as computer memory, non-transitory storage, etc. In another instance, the computer executable instructions are additionally or alternatively stored in transitory or signal medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a first ultrasound probe connector, wherein the first ultrasound probe connector comprises a first number of pins;
   a second ultrasound probe connector, wherein the second ultrasound probe connector comprises a second number of pins;
   a first ultrasound probe in communication with the first ultrasound probe connector;
   a second ultrasound probe in communication with the second ultrasound probe connector;
   a beamformer configured to beamform ultrasound signals, the beamformer, including:
      input/output configured to at least receive ultrasound signals, wherein the input/output includes a first number of channels, and the first number of channels is less than a summation of the first and second number of pins; and
   a single switch, including one side in electrical communication with elements of the first and second connectors and another side in electrical communication with the input/output, wherein the switch electrically connects, at a same time, a pin of the first ultrasound probe connector and a pin of the second ultrasound probe connector to the input/output and simultaneously routes ultrasound signals concurrently received via the pin of the first ultrasound probe connector and the pin of the second ultrasound probe connector through the input/output to the beamformer, which processes the ultrasound signals.

2. The system of claim 1, wherein the ultrasound signals correspond to ultrasound echo signals.

3. The system of claim 1, wherein the switch includes sub-switches between the first and second ultrasound probe connectors and a channel of the input/output, and further comprising:
   a switch controller that controls the sub-switches to switch so that only a single one of the signals concurrently received via the first and second ultrasound probe connectors is connected to a channel at any given moment in time based on a switching algorithm.

4. The system of claim 3, further comprising:
   a third ultrasound probe connector;
   wherein the switch concurrently routes ultrasound signals concurrently received via the first, second and third ultrasound probe connectors to the beamformer.

5. The system of claim 1, wherein the first number of channels is greater than the first number of pins and the second number of pins.

6. The system of claim 1, further comprising:
   a plurality of ultrasound probes connected to the first and second ultrasound probe connectors; and
   a mechanical probe support configured to couple the plurality of ultrasound probes together, spatially oriented offset from one another.

7. The system of claim 6, wherein the mechanical probe support is configured to support the plurality of ultrasound probes angularly offset from each other by approximately ninety degrees.

8. The system of claim 6, wherein the mechanical probe support is configured to support the plurality of ultrasound probes angularly offset from each other by approximately one hundred and eighty degrees.

9. The system of claim 6, wherein the mechanical probe support is configured to support the plurality of ultrasound probes parallel to one another.

10. The system of claim 6, wherein the plurality of probes are different types of probes.

11. The system of claim 6, wherein the plurality of probes are a same type of probe.

12. The system of claim 1, wherein the ultrasound signals correspond to ultrasound echo signals or ultrasound transducer element excitation signals.

13. A method for ultrasound imaging, comprising:
routing a first signal between a first transducer array of a first ultrasound probe connected to a first connector of an ultrasound console and input/output of a beamformer of the ultrasound console through a single switch of the ultrasound console, wherein the first ultrasound probe connector comprises a first number of pins; and
routing, simultaneously with routing the first signal, a second signal between a second transducer array of a second ultrasound probe connected to a second connector of the ultrasound console and the input/put of the beamformer through the single switch, wherein the second ultrasound probe connector comprises a second number of pins, and
wherein the input/output includes a first number of channels, and the first number of channels is less than a summation of the first and second number of pins, and the single switch includes one side in electrical communication with elements of the first and second connectors and another side in electrical communication with the input/output of the beamformer.

14. The method of claim 13, wherein the first signal and the second signal correspond to ultrasound echo signals.

15. The method of claim 13, wherein the first signal and the second signal correspond to ultrasound transducer element excitation signals.

16. The method of claim 13, wherein one of the first or second signals corresponds to an ultrasound transducer element excitation signal and the other of the first or second signal corresponds to an ultrasound echo signal.

17. The method of claim 13, further comprising:
routing, concurrently with routing the first signal, a third signal between a third transducer array of a third ultrasound probe connected to a third connector of the ultrasound console and the beamformer through the switch.

* * * * *